United States Patent [19]

Grossenbacher et al.

[11] Patent Number: 5,661,001
[45] Date of Patent: Aug. 26, 1997

[54] HIGH MOLECULAR WEIGHT DESULPHATOHIRUDIN

[75] Inventors: Hugo Grossenbacher, Olten; Jui Yoa Chang, Bubendorf; Walter Märki, Möhlin, all of Switzerland

[73] Assignee: Ciba-Geigy Corporation, Tarrytown, N.Y.

[21] Appl. No.: 406,948

[22] PCT Filed: Jul. 23, 1994

[86] PCT No.: PCT/EP94/02438

§ 371 Date: Mar. 29, 1995

§ 102(e) Date: Mar. 29, 1995

[87] PCT Pub. No.: WO95/04823

PCT Pub. Date: Feb. 16, 1995

[30] Foreign Application Priority Data

Aug. 4, 1993 [EP] European Pat. Off. ............ 93810552

[51] Int. Cl.$^6$ ..................... C07K 14/815; C12P 21/06; A61K 38/03
[52] U.S. Cl. ................... 435/69.1; 530/300; 530/324; 530/345; 514/15; 514/12
[58] Field of Search .................... 530/300, 324; 435/344, 345, 69.1, 320.1, 240.1; 536/23.1, 24.1

[56] References Cited

U.S. PATENT DOCUMENTS

| | | | |
|---|---|---|---|
| 4,572,798 | 2/1986 | Koths et al. | 260/112 |
| 4,620,948 | 11/1986 | Builder et al. | 530/419 |
| 5,236,898 | 8/1993 | Krstenansky et al. | 514/9 |

FOREIGN PATENT DOCUMENTS

| | | |
|---|---|---|
| 0143081 | 5/1985 | European Pat. Off. . |
| 0225286 | 6/1987 | European Pat. Off. . |
| 0291982 | 11/1988 | European Pat. Off. . |
| 0340170 | 11/1989 | European Pat. Off. . |
| 0341215 | 11/1989 | European Pat. Off. . |
| 0347376 | 12/1989 | European Pat. Off. . |
| WO86/05809 | 10/1986 | WIPO . |
| WO88/08003 | 10/1988 | WIPO . |
| WO88/08849 | 11/1988 | WIPO . |
| WO91/09125 | 6/1991 | WIPO . |
| WO92/05748 | 4/1992 | WIPO . |
| WO93/00363 | 1/1993 | WIPO . |

OTHER PUBLICATIONS

Steiner, V. 1988 Diploma Thesis. University of Basel, Switzerland.
Krstenansky et al 1988 Biochimica et Biophysica Acta 957:53–59.
Talbot et al 1989 Thrombosis & Haemostasis 61(1): 77–80.
Maraganore et al 1990 Biochemistry 29:7095–7101.
Altman, J.D., et al., "Intracellular Expression of BPTI Fusion Proteins and Single Column Cleavage/Affinity Purification by Chymotrypsin", *Protein Engineering*, 4(5):593–600 (1991).
Bergmeyer (ed), "Samples, Reagents, Assessment of Results", *Meth. in Enzym. Analysis*, vol. II, pp. 314–316 (1983), Verlag Chemie, Weinheim (FRG).
Börnsen, K.O., et al., "Matrix–Assisted Laser Desorption and Ionization Mass Spectrometry and Its Applications in Chemistry", *Chimia*, 44:412–416 (1990).
Botstein, D., et al., "Strategies and Applications of In Vitro Mutagenesis", *Science*, 229:1193–1201 (1985).
Braun, P.J., et al., "Use of Site–Directed Mutagenesis to Investigate the Basis for the Specificity of Hirudin", *Biochemistry*, 27:6517–6522 (1988).
Chang, J–Y, "Production, Properties, and Thrombin Inhibitory Mechanism of Hirudin Amino–terminal Core Fragments", *J. Biol. Chem.*, 265(36):22159–22166 (1990).
Chang, J–Y, et al., "Direct Analysis of the Disulfide Content of Proteins: Methods for Monitoring the Stability and Refolding Process of Cystine–Containing Proteins", *Anal. Biochem.*, 197:52–58 (1991).
Chang, J–Y, et al., "Production of Disulfide–linked Hirudin Dimer by In Vitro Folding", *FEBS Letters*, 336(1):53–56 (1993).
Chatrenet, B., et al., "The Folding of Hirudin Adopts a Mechanism of Trial and Error", *J. Biol. Chem.*, 267(5):3038–3043 (1992).
Dodt, J., et al., "The Complete Amino Acid Sequence of Hirudin, A Thrombin Specific Inhibitor", *FEBS Letters*, 165(2):180–184 (1984).
Gardella, T.J., et al., "Expression of Human Parathyroid Hormone–(1–84) in *Escherichia coli* as a Factor X–cleavable Fusion Protein", *J. Biol. Chem.*, 265(26):15854–15859 (1990).
Grütter, M.G., et al., "Crystal Structure of the Thrombin–hirudin Complex: A Novel Mode of Serine Protease Inhibition":, *The EMBO Journal*, 9(8):2361–2365 (1990).
Halenbeck, R., et al., "Renaturation and Pruification of Biologically Active Recombinant Human Macrophage Colony–Stimulating Factor Expressed in *E. coli*", *Biotechnology*, 7:710–715 (1989).
Hinnen, A., "Transformation of Yeast", *PNAS*, 75(4):1929–1933 (1978).
Markwardt, F., et al., "Pharmacological Studies on the Antithrombotic Action of Hirudin in Experimental Animals", *Thromb. Haemost.*, 47(3):226–229 (1982).
Meyhack, B., et al., "Desulfatchirudin, a Specific Thrombin Inhibitor: Expression and Secretion in Yeast", *Thromb. Res. Suppl.*, VII:33 (1987).

(List continued on next page.)

Primary Examiner—Vasu S. Jagannathan
Assistant Examiner—Karen Cochrane Carlson
Attorney, Agent, or Firm—Gregory D. Ferraro

[57] ABSTRACT

The invention pertains to the field of thrombin inhibitors and describes the production of modified desulphatohirudins, particularly desulphatohirudins, with the aid of genetic engineering. The present invention is also directed to a method for the denaturation and renaturation of a modified desulphatohirudin to a biologically active thrombin inhibitor and the combination of two or more of desulphatohirudins to form higher molecular weight thrombin inhibitors.

33 Claims, 1 Drawing Sheet

OTHER PUBLICATIONS

Narang, S.A., "DNA Synthesis", *Tetrahedron*, 39(1):3–22 (1983).

Nishikawa, S. et al., "Efficient Cleavage by α–thrombin of a Recombinant Fused Protein which Contains Insulin–like Growth Factor I", *Protein Engineering*, 1(6):487–492 (1987).

Norris, K., et al., "Efficient Site–directed Mutagenesis by Simultaneous Use of Two Primers", *Nucleic Acids Research*, 11(15):5103–5112 (1983).

Sabin, E.A., et al., "High–level Expression and In Vivo Processing of Chimeric Ubiquitin Fusion Proteins in *Saccharomyces cerevisiae*", *Biotechnology*, 7:705–709 (1989).

Scharf, M., et al., "Primary Structures of New Iso–hirudins", *FEBS Letters*, 255(1):105–110 (1989).

Steiner, V., et al., "Primary Structure and Function of Novel O–Glycosylated Hirudins from the Leech", *Biochemistry*, 31:2294–2298 (1992).

Stone, S.R., et al., "Kinetics of the Inhibition of Thrombin by Hirudin", *Biochemistry*, 25:4622–4628 (1986).

Wallace, A., et al., "Contribution of the N–Terminal Region of Hirudin to its Interaction with Thrombin", *Biochemistry*, 28:10079–10084 (1989).

Zoller, M.J., et al., "Oligonucleotide–Directed Mutagenesis of DNA Fragments Cloned into M13 Vectors", *Methods Enzymol.*, 100:468–500 (1983).

Figure 1

SEQUENCE LISTING ( 1 ) GENERAL INFORMATION:

( i i i ) NUMBER OF SEQUENCES: 8

( 2 ) INFORMATION FOR SEQ ID NO: 1:

( i ) SEQUENCE CHARACTERISTICS:
        ( A ) LENGTH: 24 base pairs
        ( B ) TYPE: nucleic acid
        ( C ) STRANDEDNESS: single
        ( D ) TOPOLOGY: linear     ( i i ) MOLECULE TYPE: DNA (genomic)

( i x ) FEATURE:
        ( A ) NAME/KEY: misc_feature
        ( B ) LOCATION: 1..24
        ( D ) OTHER INFORMATION: /product="Synthetical PCR Primer"

( x i ) SEQUENCE DESCRIPTION: SEQ ID NO: 1:

TCGGTCGACG CTCTCCCTTA TGCG       24

( 2 ) INFORMATION FOR SEQ ID NO: 2:

( i ) SEQUENCE CHARACTERISTICS:
        ( A ) LENGTH: 31 base pairs
        ( B ) TYPE: nucleic acid
        ( C ) STRANDEDNESS: single
        ( D ) TOPOLOGY: linear     ( i i ) MOLECULE TYPE: DNA (genomic)

( i x ) FEATURE:
        ( A ) NAME/KEY: misc_feature
        ( B ) LOCATION: 1..31
        ( D ) OTHER INFORMATION: /product="Synthetical PCR Primer"

( x i ) SEQUENCE DESCRIPTION: SEQ ID NO: 2:

TTGGGTTCTT GTGGTGAAAA GAACCAATGT G       31

( 2 ) INFORMATION FOR SEQ ID NO: 3:

( i ) SEQUENCE CHARACTERISTICS:
        ( A ) LENGTH: 31 base pairs
        ( B ) TYPE: nucleic acid
        ( C ) STRANDEDNESS: single
        ( D ) TOPOLOGY: linear     ( i i ) MOLECULE TYPE: DNA (genomic)

( i x ) FEATURE:
        ( A ) NAME/KEY: misc_feature
        ( B ) LOCATION: 1..31
        ( D ) OTHER INFORMATION: /product="Synthetical PCR Primer"

( x i ) SEQUENCE DESCRIPTION: SEQ ID NO: 3:

CTTTTCACCA CAAGAACCCA AGATACACTT G       31

( 2 ) INFORMATION FOR SEQ ID NO: 4:

( i ) SEQUENCE CHARACTERISTICS:
        ( A ) LENGTH: 26 base pairs
        ( B ) TYPE: nucleic acid
        ( C ) STRANDEDNESS: single
        ( D ) TOPOLOGY: linear     ( i i ) MOLECULE TYPE: DNA (genomic)

( i x ) FEATURE:
        ( A ) NAME/KEY: misc_feature (B) LOCATION: 1..26
(D) OTHER INFORMATION: /product="Synthetical PCR Primer"

(x i) SEQUENCE DESCRIPTION: SEQ ID NO: 4:

GCCAAGCTTG GCTGCAGATT TTAATC                                         26

(2) INFORMATION FOR SEQ ID NO: 5:

(i) SEQUENCE CHARACTERISTICS:
    (A) LENGTH: 1130 base pairs
    (B) TYPE: nucleic acid
    (C) STRANDEDNESS: single
    (D) TOPOLOGY: linear (i i) MOLECULE TYPE: DNA (genomic)

(i x) FEATURE:
    (A) NAME/KEY: misc_signal
    (B) LOCATION: 1..1130
    (D) OTHER INFORMATION: /function="first 1130 nucleotides
        of pJDB207/GAPFL-YHIR (EP-A-340 170)"

(i x) FEATURE:
    (A) NAME/KEY: misc_feature
    (B) LOCATION: 1..276
    (D) OTHER INFORMATION: /product="SalI - BamHI fragment of
        pBR322"

(i x) FEATURE:
    (A) NAME/KEY: misc_feature
    (B) LOCATION: 277..284
    (D) OTHER INFORMATION: /function="BamHI/BglII linker"

(i x) FEATURE:
    (A) NAME/KEY: promoter
    (B) LOCATION: 285..478
    (D) OTHER INFORMATION: /function="GAPFL promoter"

(i x) FEATURE:
    (A) NAME/KEY: misc_feature
    (B) LOCATION: 479..484
    (D) OTHER INFORMATION: /product="EcoRI linker"

(i x) FEATURE:
    (A) NAME/KEY: misc_signal
    (B) LOCATION: 488..538
    (D) OTHER INFORMATION: /function="PHO5 signal sequence"

(i x) FEATURE:
    (A) NAME/KEY: mat_peptide
    (B) LOCATION: 539..733
    (D) OTHER INFORMATION: /product="Hirudin HV1"
        / standard_name="HV1"

(i x) FEATURE:
    (A) NAME/KEY: terminator
    (B) LOCATION: 737..1113
    (D) OTHER INFORMATION: /standard_name="PHO5 terminator"

(i x) FEATURE:
    (A) NAME/KEY: misc_feature
    (B) LOCATION: 1117..1122
    (D) OTHER INFORMATION: /function="M13 cloning site"

(i x) FEATURE:
    (A) NAME/KEY: misc_signal
    (B) LOCATION: 734..736
    (D) OTHER INFORMATION: /function="Translation terminator"
        / standard_name="TAG"

(x i) SEQUENCE DESCRIPTION: SEQ ID NO: 5:

GTCGACGCTC TCCCTTATGC GACTCCTGCA TTAGGAAGCA GCCCAGTAGT AGGTTGAGGC     60

CGTTGAGCAC CGCCGCCGCA AGGAATGGTG CATGCAAGGA GATGGCGCCC AACAGTCCCC    120

CGGCCACGGG GCCTGCCACC ATACCCACGC CGAAACAAGC GCTCATGAGC CCGAAGTGGC    180

-continued

| | | | | | |
|---|---|---|---|---|---|
| GAGCCCGATC | TTCCCCATCG | GTGATGTCGG | CGATATAGGC | GCCAGCAACC | GCACCTGTGG | 240
| CGCCGGTGAT | GCCGGCCACG | ATGCGTCCGG | CGTAGAGGAT | CTCCCTGAAA | AAAAAGGTTG | 300
| AAACCAGTTC | CCTGAAATTA | TTCCCCTACT | TGACTAATAA | GTATATAAAG | ACGGTAGGTA | 360
| TTGATTGTAA | TTCTGTAAAT | CTATTTCTTA | AACTTCTTAA | ATTCTACTTT | TATAGTTAGT | 420
| CTTTTTTTTA | GTTTAAAAC | ACCAAGAACT | TAGTTTCGAA | TAAACACACA | TAAATAAAGA | 480
| ATTCAAAATG | TTTAAATCTG | TTGTTTATTC | AATTTTAGCC | GCTTCTTTGG | CCAATGCAGT | 540
| TGTTTACACC | GACTGTACCG | AATCTGGTCA | AAACTTGTGT | TGTGTGAAG | GTTCTAACGT | 600
| TTGTGGTCAA | GGTAACAAGT | GTATCTTGGG | TTCTGACGGT | GAAAGAACC | AATGTGTTAC | 660
| CGGTGAAGGT | ACCCCAAAGC | CACAATCTCA | CAACGACGGT | GACTTCGAAG | AAATCCCAGA | 720
| AGAATACTTG | CAATAGGATC | CTGGTACGTT | CCTCAAGGTG | CTCGTGTCTA | CACCGAAAAA | 780
| TTCCAATGTT | CTAACGACAC | CTACGTCAGA | TACGTCATTA | ACGATGCTGT | TGTTCCAATT | 840
| GAAACCTGTT | CCACTGGTCC | AGGGTTCTCT | TGTGAAATCA | ATGACTTCTA | CGACTATGCT | 900
| GAAAAGAGAG | TAGCCGGTAC | TGACTTCCTA | AAGGTCTGTA | ACGTCAGCAG | CGTCAGTAAC | 960
| TCTACTGAAT | TGACCTTCTA | CTGGGACTGG | AACACTACTC | ATTACAACGC | CAGTCTATTG | 1020
| AGACAATAGT | TTTGTATAAC | TAAATAATAT | TGGAAACTAA | ATACGAATAC | CCAAATTTTT | 1080
| TATCTAAATT | TTGCCGAAAG | ATTAAAATCT | GCAGCCAAGC | TTTGAAGAAA | | 1130

( 2 ) INFORMATION FOR SEQ ID NO: 6:

( i ) SEQUENCE CHARACTERISTICS:
        ( A ) LENGTH: 65 amino acids
        ( B ) TYPE: amino acid
        ( C ) STRANDEDNESS: single
        ( D ) TOPOLOGY: linear     ( i i ) MOLECULE TYPE: protein     ( i x ) FEATURE:
        ( A ) NAME/KEY: Protein
        ( B ) LOCATION: 1..65
        ( D ) OTHER INFORMATION: /note="hirudin variant 1 (HV1)"

( x i ) SEQUENCE DESCRIPTION: SEQ ID NO: 6:

```
Val  Val  Tyr  Thr  Asp  Cys  Thr  Glu  Ser  Gly  Gln  Asn  Leu  Cys  Leu  Cys
 1                   5                        10                       15

Glu  Gly  Ser  Asn  Val  Cys  Gly  Gln  Gly  Asn  Lys  Cys  Ile  Leu  Gly  Ser
               20                        25                       30

Asp  Gly  Glu  Lys  Asn  Gln  Cys  Val  Thr  Gly  Glu  Gly  Thr  Pro  Lys  Pro
          35                        40                       45

Gln  Ser  His  Asn  Asp  Gly  Asp  Phe  Glu  Glu  Ile  Pro  Glu  Glu  Tyr  Leu
     50                        55                       60

Gln
65
```

( 2 ) INFORMATION FOR SEQ ID NO: 7:

( i ) SEQUENCE CHARACTERISTICS:
        ( A ) LENGTH: 195 base pairs
        ( B ) TYPE: nucleic acid
        ( C ) STRANDEDNESS: single
        ( D ) TOPOLOGY: linear     ( i i ) MOLECULE TYPE: DNA (genomic)

( i x ) FEATURE:
        ( A ) NAME/KEY: mat_peptide
        ( B ) LOCATION: 1..195

(D) OTHER INFORMATION: /product="[33-Cys]HV1"

(xi) SEQUENCE DESCRIPTION: SEQ ID NO: 7:

| | | | | | |
|---|---|---|---|---|---|
| GTTGTTTACA | CCGACTGTAC | CGAATCTGGT | CAAAACTTGT | GTTTGTGTGA | AGGTTCTAAC | 60
| GTTTGTGGTC | AAGGTAACAA | GTGTATCTTG | GGTTCTTGTG | GTGAAAAGAA | CCAATGTGTT | 120
| ACCGGTGAAG | GTACCCCAAA | GCCACAATCT | CACAACGACG | GTGACTTCGA | AGAAATCCCA | 180
| GAAGAATACT | TGCAA | | | | | 195

(2) INFORMATION FOR SEQ ID NO: 8:

(i) SEQUENCE CHARACTERISTICS:
(A) LENGTH: 65 amino acids
(B) TYPE: amino acid
(C) STRANDEDNESS: single
(D) TOPOLOGY: linear (ii) MOLECULE TYPE: protein (ix) FEATURE:
(A) NAME/KEY: Protein
(B) LOCATION: 1..65
(D) OTHER INFORMATION: /note="[33-Cys]HV1"

(xi) SEQUENCE DESCRIPTION: SEQ ID NO: 8:

Val Val Tyr Thr Asp Cys Thr Glu Ser Gly Gln Asn Leu Cys Leu Cys
1               5                   10                  15

Glu Gly Ser Asn Val Cys Gly Gln Gly Asn Lys Cys Ile Leu Gly Ser
            20                  25                  30

Cys Gly Glu Lys Asn Gln Cys Val Thr Gly Glu Gly Thr Pro Lys Pro
        35                  40                  45

Gln Ser His Asn Asp Gly Asp Phe Glu Glu Ile Pro Glu Glu Tyr Leu
    50                  55                      60

Gln
65

HIGH MOLECULAR WEIGHT DESULPHATOHIRUDIN

The invention pertains to the field of thrombin inhibitors and describes the production of modified hirudins more especially desulphatohirudin muteins, with the aid of genetic engineering. It is a further object of the invention to provide a method for the preparation of biologically active high molecular weight hirudin by combining two to four monomers of said hirudins.

The hirudins are anticoagulant agents that occur naturally in leeches (e.g. in medicinal leech *Hirudo medicinalis*). The hirudins are equally acting polypeptides having an accumulation of hydrophobic amino acids at the N-terminus and of polar amino acids at the C-terminus, three disulfide bridges and the anticoagulant activity in common. A characteristic feature of most natural hirudins is the presence of a tyrosine sulphate residue at the C-terminal part ($Tyr^{63}$) of the molecules. Apart from the well-known hirudin variants HV1, HV2 and HV3 additional hirudins have been reported to exist in nature, see, for example, M. Scharf et al. FEBS Lett. 255, 105–110 (1989), supporting the concept of hirudins as a family of isoinhibitors.

The hirudins, for example hirudin variant 1 (HV1), are the most potent and most specific known inhibitors of thrombin, the serine protease that catalyzes the final step (the conversion of the zymogen fibrinogen in clottable fibrin) in blood coagulation. Other enzymes of the blood coagulation cascade are not inhibited by hirudins. In contrast to heparin which is the preferred anticoagulant in conventional anticoagulation therapy, the hirudins exert their inhibiting action directly on thrombin and, unlike the former, do not act through antithrombin III. The only pharmacologically detectable effect of purified hirudins is the inhibition of blood coagulation and the prophylaxis of thrombosis. No side effects, such as effects on heart rate, respiration, blood pressure, thrombocyte count, fibrinogen and hemoglobin, have been observed after intravenous administration of hirudins to dogs, even in high doses. In a series of animal models hirudins have proved effective in experimental thrombosis (induced either by stasis or by the injection of thrombin), in endotoxin shock, and also in DIC (disseminated intravascular coagulation). Whenever direct comparison tests have been carried out, hirudins have proved to be superior to heparin.

In recent years cDNAs and synthetic genes coding for hirudin variants have been cloned and expressed in microbial hosts, such as *Escherichia coli* and, in particular, *Saccharomyces cerevisiae*. Although the expression products lack the sulphate monoester group at $Tyr^{63}$- and were therefore designated "desulphatohirudins"—they turned out to exhibit essentially the same biological activity as the natural sulphated hirudins.

A characteristic of the therapeutic application of recombinant desulphatohirudin is its half-life in the circulation of about 50 min. and therefore, the rapid excretion from the human body. The reason for the rapid excretion is the filtration of the glomerulum in the kidney for substances having a molecular weight below 70 000. Because of this rapid excretion, the daily dose of desulphatohirudin is administered normally in two or more separate portions. One strategy to obtain longer acting thrombin inhibitors is to synthesize high molecular weight hirudins. In WO 91/08229 the conjugation of hirudin with polyalkylenglycol is described. As the polyalkylenglycols are normally very heterogeneous in molecular size and weight, their combination with hirudin leads to a heterogeneous mixture and the administration of a defined dose of hirudin is difficult. In another approach the hirudin is crosslinked with other proteins like albumin (WO 92/05748). These kinds of conjugates show diminished activities and increased immunogenic properties and are therefore unsuitable for long term administration.

In WO 91/09125 relatively inactive fusion proteins are described that have to be activated by enzymes of the clotting cascade to have fibrinolytic or clot formation inhibition activity.

Surprisingly it has now been found that conjugates consisting of two to four residues of desulphatohirudin muteins or desulphatohirudin derivatives have a significantly increased plasma half life even if the molecular weight is considerably lower than the critical value of about 70 000, see above, surprisingly show no detectable increased immunogenic properties, do not have to be cleaved by an enzyme involved in blood clotting and have an unchanged activity. With this increased plasma half life the administration of the daily dose of desulphatohirudin in a single portion is possible.

Accordingly, the present invention relates to a conjugate essentially consisting of two to four residues of desulphatohirudin muteins or derivatives wherein the conjugate is no fusion protein and the residues of desulphatohirudin muteins or derivatives having hirudin activity are not connected via glutaraldehyde or carbodiimide.

The term "desulphatohirudin" is intended to embrace all desulphatohirudin compounds described in literature or obtainable from a transformed microorganism strain containing DNA which codes for a desulphatohirudin or a derivative thereof. Such desulphatohirudins are, for example, desulphatohirudin derivatives HV 1, HV2 and HV3 (PA), as well as other hirudin and hirullin proteins as described by M. Scharf et al. (FEBS Lett: (1989), 255, 105–110) and EP-A-347 376. It is to be understood that hirudin derivatives or shorter fragments having hirudin activity (i.e. having a thrombin inhibiting and/or thrombin binding action) are also covered by the term "desulphatohirudin". Such fragments and derivatives are, for example, C-terminally shortened desulphatohirudins, i.e. desulphatohirudins lacking up to seven amino acids at the C-terminus.

The desulphatohirudins or active fragments or derivatives thereof can be modified by a linkage of a further reactive group, wherein the reactive group shows a biological effect on the thrombin activity. It is for example possible to combine the thrombin binding domain of desulphatohirudin that is located in the C-terminal part with a chemically synthesized thrombin inhibitor. Examples for such chemically modified desulphatohirudin derivatives are hirulogs (WO 90/04642).

In a preferred embodiment a conjugate according to the invention essentially consists of two residues of desulphatohirudin muteins or derivatives. The components of the conjugates according to the invention, i.e. the residues of desulphatohirudin muteins or derivatives, may be the same or different.

The desulphatohirudin muteins or derivatives are connected directly or via a linker group. For this purpose normally one or more, preferred is one, genuine amino acid of desulphatohirudin is replaced by one or more radicals capable of being crosslinked, e.g., an amino acid bearing a reactive side chain.

It is an object of the invention to provide a desulphatohirudin mutein or derivative capable of building conjugates, essentially conjugates consisting of two to four residues of such desulphatohirudins. In a preferred embodiment of the invention one or more genuine amino acids of a desulphatohirudin mutein or derivative are replaced by an amino acid selected from the group consisting of aspartic acid, glutamic acid, lysine and cysteine.

The replacement of one amino acid is preferred, more preferred is the replacement of a single amino acid by cysteine and most preferred the replacement of Asp$^{33}$ in desulphatohirudin HV1 by cysteine.

A conjugate consisting of two desulphatohirudin residues can be produced by forming a peptide bond between aspartic acid or glutamic acid in one residue and lysine in the other residue, or preferred a disulfide bond between two cysteine residues.

In the alternative, the components of the conjugate according to the invention (two to four residues of desulphatohirudin mutein or desulphatohirudin derivatives) may also be connected via a linker group. To this end, desulphatohirudin muteins or derivatives are linked via the reactive side chain, e.g., of the introduced amino acid as defined above to a linker molecule which has two or more reactive groups, two reactive groups being preferred, said reactive groups being capable of reacting and forming a covalent bond with the reactive side chain of the desulphatohirudin mutein or derivative. Such linker molecules are molecules beating two or more reactive groups like —SH, —N$_3$, —COOH, —COBr, —COCl, —NH$_2$, —CHO, —CO—O—CO—, —CO—NH—CO—. Examples are N-5-azido-2-nitrobenzoyloxysuccinimide, p-azidophenazylbromide, p-azidophenyl glyoxal, N-4-(azidophenylthio)phthalimide, bis(sulfosuccinimidyl) suberate, bis-maleimidohexane, bis[2-(succinimidooxycarbonyloxy)ethyl] sulfone, 1,5-difluoro-2,4-dinitrobenzene, 4,4'-diisothiocyano-2,2'-disulfonic acid stilbene, dimethyl adipimidate, dimethyl pimelimidate, dimethyl suberimidate, dithiobis(succinimidylpropionate), disuccinimidyl suberate, disuccinimidyl tatrate, dimethyl 3,3'-dithiobispropionimidate, 4,4'-dithiobisphenylazide, 3,3'-dithiobis(succinimidylpropionate), ethyl-4-azidophenyl-1,4-dithiobutyrimidate, 1-azido-4-fluoro-3-nitrobenzene, N-hydroxysuccinimidyl-4-azidobenzoate, methyl-4-azidobenzoimidate, m-maleimidobenzoyl-N-hydroxysulfosuccinimide ester, N-hydroxysuccinimidyl-4-azidosalicylic acid, p-nitrophenyl-2-diazo-3,3,3-trifluoro propionate, N-succinimidyl(4-azidophenyl)-1,3'-dithiopropionate, sulfosuccinimidyl 2-(m-azido-o-nitrobenzamido)-ethyl-1,3'-dithiopropionate, N-succinimidyl-6(4'-azido-2'-nitrophenylamino)hexanoate, sulfosuccinimidyl 2-(p-azidosalicylamido)ethyl-1,3'-di-thiopropionate, N-succinimidyl(4-iodoacetyl)aminobenzoate, succinimidyl 4-(N-maleimidomethyl)-cyclohexane-1-carboxylate, succinimidyl 4-(p-meleimidophenyl)-butyrate, N-succinimidyl 3-(2-pyridyldithio)propionate, bis[2-(sulfosuccinimidooxycarbonyloxy)ethyl]sulfone, disulfosuccinimidyl tatrate, ethylene glycolbis(sulfosuccinimidylsuccinate), m-maleimidobenzoyl-N-hydroxysulfosuccinate), sulfosuccinimidyl (4-azidophenyldithio)-propionate, sulfosuccinimidyl 6-(4'azido-2'-nitrophenylamino)hexanoate, sulfosuccinimidyl (4-iodoacetyl)aminobenzoate, sulfosuccinimidyl 4-(N-maleimidomethyl)cyclohexane-1-carboxylate, sulfosuccinimidyl 4-(p-maleimidophenyl)butyrate and 2-iminothiolane.

Preferred linker molecules specifically react with —SH groups of amino acids, e.g., dithio compounds like dithioerythrol, dithiothreitol, dimercaptobenzene, 1,4-butandithiole, 1,3-propanedithiol, short amino acid chains beating two cysteins or other —SH crosslinking agents like bis-maleimidohexane, m-maleimidobenzoyl-N-hydroxysulfosuccinimide ester, N-succinimidyl(4-iodoacetyl)aminobenzoate, succinimidyl 4-(N-maleimidomethyl)-cyclohexane-1-carboxylate, succinimidyl 4-(p-meleimidophenyl)-butyrate, N-succimimidyl 3-(2-pyridyldithio)propionate, m-maleimidobenzoyl-N-hydroxysulfosuccinyte).

The amino acid exchange and therefore, the attachment to another desulphatohirudin or to a linker is done in a region not essential for the activity of desulphatohirudin. Desulphatohirudin contains two functional domains which bind to independent sites of α-thrombin; a compact N-terminal core domain binding to the catalytic site of thrombin (Chang et al., J. Biol. Chem. (1990), 265, 22159–22166) and a disordered terminal tail which is complementary to the exosite (fibrinogen recognition site) of the enzyme Maraganore et at., J. Biol. Chem. (1989), 264, 8692–8698). Linking two monomers through the C-terminal region is not desirable as nearly every amino acid residue inside this domain is required for the full potency of desulphatohirudin (Chang, J. Biol. Chem. (1990), 265, 22159–22166). Within the N-terminal domain, however, there is a flexible loop (residues 30 to 40, especially residues 31 to 36) which is located on the surface and is distant from the thrombin binding site (Grütter et al., EMBO (1990), 9, 2361–2365). The alteration of the desulphatohirudin monomers and the connection of the desulphatohirudin monomers to form the conjugates according to the invention is preferably done in the region between amino acid residues 7 to 50, more preferably 30 to 40 and especially between residues 31 to 36. Most preferred is a desulphatohirudin HV1 wherein Asp$^{33}$ is replaced by cysteine. Therefore the monomers of the desulphatohirudin muteins or derivatives, or the monomer of desulphatohirudin mutein or derivative and the linker group, are preferably linked in the region between amino acid residues 7 to 50, more preferably 30 to 40, and most preferably between residues 31 to 36.

Due to the amino acid exchange, the folding of the nascent modified desulphatohirudin chain may be different to the folding of the unmodified desulphatohirudin. If the native desulphatohirudin structure is not formed spontaneously, the isolated desulphatohirudin may be denaturated and refolded under suitable conditions to a configuration that shows thrombin inhibiting activities.

A number of publications have appeared which report refolding attempts for individual proteins produced in bacterial hosts, or which are otherwise in a denatured or non-native form. Formation of a dimeric, biologically active human colony stimulating factor-1 (CSF-1) after expression in E. coli is described in WO 88/8003 and by Halenbeck, R. et al. Biotechnologie (1989), 7, 710–715. The procedures described involve the steps of initial solubilization of CSF-1 monomers isolated from inclusion bodies under reducing conditions in a chaotropic environment comprising urea or guanidine hydrochloride, refolding which is achieved by stepwise dilution of the chaotropic agents, and final oxidation of the refolded molecule in the presence of a redoxsystem. In WO 88/8849 a process for recovering recombinant interleukin-2 (IL-2) is disclosed, characterized in that IL-2 isolated from refractile bodies is denatured under reducing conditions with 6M guanidine hydrochloride, the soluble IL-2 is oxidized by a controlled oxidation in the presence of Cu$^{2+}$ ions, and the oxidized IL-2 refolded by reducing the concentration of the denaturant in the solution. Interleukin-2 and interferon-β have been refolded using SDS for solubilization and Cu$^{2+}$ ions as oxidation promoters of the fully reduced protein (U.S. Pat. No. 4,572,798). The process for isolating recombinant refractile proteins as described in U.S. Pat. No. 4,620,948 involves strong denaturing agents to solubilize the proteins, reducing conditions to facilitate correct folding and denaturant replacement in presence of air or other oxidizing agents to reform the disulfide bonds. A method for renaturing unfolded proteins including cytochrome c, ovalbumin and trypsin inhibitor by reversibly binding of the denatured protein to a solid matrix and stepwise renaturing it by diluting the denaturant is disclosed in WO 86/5809. The foregoing references are merely representative of a huge amount of literature dealing with the refolding of non-native proteins derived from different sources. The man skilled in the art on the other hand knows that the success of refolding experiments cannot be predicted. Unsuccessful experiments are usually not reported. There is no certainty that anyone of the reported refolding conditions would work at all with a given denatured protein such as desulphatohirudin, muteins or derivatives. Considering the fact, that unmodified desulphatohirudin contains 6 cysteine residues and desulphatohirudin HV1 wherein $Asp^{33}$ is replaced by cysteine contains 7 cysteine residues per chain and a number of intramolecular disulfide bonds, which are required for activity, it is a particularly difficult challenge to produce biologically active polymeric and especially dimeric desulphatohirudin from its monomeric, denatured or otherwise non-native form.

It is therefore an object of the invention to provide a method for unfolding and refolding desulphatohirudin muteins or derivatives to a biologically active polymeric and especially dimeric form comprising the steps:

denaturing of desulphatohirudin as defined above with chaotropic agent, renaturing of desulphatohirudin under refolding conditions, and, if required linking of the desulphatohirudins by means of a linker, or directly.

Chaotropic agents which in suitable concentration are capable of effectively denaturing proteins by changing the spatial configuration of the respective protein through alterations at the surface thereof, either through altering the state of hydration, the solvent environment, or the solvent-surface interaction in aqueous solution and are well known in the art. Examples of such chaotropic agents or denaturants include urea, guanidine hydrochloride, sodium thiocyanate at concentrations in the range of about 4 to 9M, and detergents such as SDS, which are supplied in concentrations in the order of 0.01 to 2%. Also, acidification of the aqueous solution to a pH below 4 or basic conditions of a pH above 10 and elevated temperatures will result in denaturation of the monomer.

The term "refolding conditions" refers to buffer conditions wherein the denatured monomer is permitted to assume a conformation associated with biological activity. Conventional buffer systems such as Tris, phosphate, carbonate or citrate buffers can be used at a pH range of about 6 to 10. Under refolding conditions disulfide bond formation is promoted. Such conditions include, e.g., the presence of a solubilizing agent and a redox system which permits the continuous oxidation and reduction of the thiol/disulfide pairs. The buffer system may additionally contain suitable salts.

Suitable solubilizing agents are detergents, preferably mild detergents, organic, water-miscible solvents, or phospholipids or mixtures thereof.

Suitable redox systems which encourage the formation of disulfides are, e.g., low molecular weight sulfhydryl/ disulfide reagent combinations such as glutathione in its oxidized and reduced form, dithiotreitol in its oxidized and reduced form, β-mercaptoethanol or β-mercaptomethanol in its oxidized and reduced form, cysteine and its reduced form, and cystamine and its reduced form at concentrations of about 1 to 100 mM, especially of about 1 to 10 mM. Alternatively, thioredoxin or disulfideisomerases at a concentration of about 10 to 1000 µg/ml, especially 50 to 200 µg/ml can be used instead of the low molecular weight sulfhydryl/disulfide system.

Optionally, to further promote intermolecular and intramolecular disulfide formation, an effective amount of an oxidation promoting agent containing $Cu^{2+}$ ions (such as $CuCl_2$, $Cu(NO_3)_2$ or o-phenanthroline/$Cu^{2+}$ complexes) or $Fe^{3+}$ ions (such as $FeCl_3$ or $Fe_2(SO_4)_3$) might be added to the refolding buffer. An effective amount is the amount which at minimum will be necessary to conduct the oxidation of sulfhydryl groups within a convenient time period and which is approximately equivalent to the concentration of free sulfhydryl groups in the desulphatohirudin muteins or derivatives, which are destined to be involved in forming the desired disulfide bonds. Preferable mounts range between 0.001 to 100 µM.

Furthermore, $O_2$ or air may be bubbled through the refolding buffer either in presence or absence of oxidation promoting agents. Oxidation may also be performed using $I_2$ or benzoquinone derivatives.

In the case of desulphatohirudin variant 1 wherein, e.g., $Asp^{33}$ is replaced by cysteine ($[Cys^{33}]HV1$) the denaturation, folding and dimerization steps are usually carried out after isolation of the desulphatohirudin by methods known per se to obtain a homogenous product. The initial isolated desulphatohirudin is, e.g., denatured by addition of guanidine hydrochloride under reducing conditions, refolded by removal of the guanidine hydrochloride under alkaline conditions and subsequently the $[Cys^{33}]HV1$ monomers are oxidized and simultaneously dimerized to the $[Cys^{33}]HV1$—$[Cys^{33}]HV1$ dimers.

Both the $Cys^{33}$ monomer and the dimer are highly active anticoagulants and their potencies of thrombin inhibition are nearly indistinguishable (±3%). This suggests that one desulphatohirudin dimer binds to two molecules of α-thrombin.

In the case of a synthetic linker the monomers of the refolded desulphatohirudin muteins or derivatives can be attached to the linker by manners known pre se. Reactive amino acids that should not bind to the linker can be protected by usual protective groups as described for example in "Protective Groups in Organic Chemistry", Plenum Press, London, New York 1973, in "Methoden der organischen Chemie", Houben-Weyl, 4th Edition, Vol. 15/1, Georg-Thieme-Verlag, Stuttgart 1974, and in Th. W. Greene, "Protective Groups in Organic Synthesis", John Wiley & Sons, New York 1981. It is characteristic of protecting groups that they can be readily removed, that is to say without undesired secondary reactions taking place, for example by solvolysis, reduction or photolysis.

The alterations in the amino acid sequence of desulphatohirudin mutein or derivatives can be made by site directed mutagenesis, if the introduction of genetically encoded amino acids is desired. Otherwise, at least the part of desulphatohirudin mutein or derivative bearing the alteration has to be synthesized chemically, e.g., by fixing a first genetically synthesized part of the desulphatohirudin mutein or derivative to a solid phase and adding the missing radicals to the fixed polypeptide, in a manner known per se.

For convenience, modification of desulphatohirudin, i.e., alteration of an amino acid, is not done at the protein level. Instead, it is advantageous to modify the gene coding for desulphatohirudin by site directed mutagenesis in such a way that upon expression of said modified gene by a host the desired desulphatohirudin mutein is produced in which one or more of the amino acids is (are) replaced by one or more amino acids capable of forming bonds to a further desulphatohirudin or a linker. In a preferred embodiment a single amino acid is replaced by cysteine.

The method for the production of desulphatohirudin mutein according to the invention comprises culturing under appropriate nutrient conditions transformed host cells containing a DNA sequence coding for a hirudin mutein in which one or more of the amino acids is (are) replaced by one or more amino acids capable of forming bonds to a further desulphatohirudin or a linker, and isolating said desulphatohirudin mutein.

Suitable host cells are, e.g., bacteria, such as *E. coli*, or eukaryotic host cells, e.g., yeast, such as *Saccharomyces cerevisiae*. The preferred host organism according to the present invention is *Saccharomyces cerevisiae*.

The host cells, especially yeast, containing the above DNA sequence are cultured using methods known in the art.

The DNAs including the sequences as shown in SEQ ID NO: 5 and 7 can be manufactured by methods known in the art. The methods for the manufacture of these DNA include chemically synthesizing the DNA, excising a portion of the DNA comprising the codon for the undesired amino acid residue from the genuine hirudin gene and replacing it with a DNA segment wherein said codon has been substituted with a deoxyribonucleotide triplet coding for the desired amino acid residue, or accomplishing the deoxyribonucleotide substitution by means of site-directed mutagenesis.

The chemical synthesis of DNA is well-known in the art and makes use of conventional techniques. Appropriate techniques have been compiled by S. A. Narang (Tetrahedron (1983), 39, 3). In particular, the methods are described in EP-A-146 785.

Excision of a portion of the mature hirudin DNA may be effected by using restriction enzymes. A prerequisite of this method is the availability of appropriate restriction sites in the vicinity of the codon to be altered. A small restriction fragment containing the codon for an undesired amino acid is removed by endonuclease cleavage. A corresponding double stranded DNA sequence is prepared, for example by means of chemical synthesis, in which triplets coding for the desired amino acid are used. The DNA fragment is ligated in the proper orientation to the remaining large fragment to yield a double stranded DNA sequence coding for a desulphatohirudin mutein. For convenience and in order to facilitate handling of the hirudin gene the latter is advantageously contained in a greater DNA segment provided with appropriate linkers which allow insertion and cloning of the segment in a cloning vector.

In a preferred embodiment of the present invention the preparation of DNAs having the DNA sequences according to SEQ ID NO: 7 is effected by site-directed mutagenesis. This method is an in vitro mutagenesis procedure by which a defined site within a region of cloned DNA can be altered (cf. the review articles of M. J. Zoller and M. Smith, Methods Enzymol. (1983), 100, 468; D. Botstein and D. Shortle, Science (1985), 229, 1193).

The method of mutating the wild-type hirudin gene is characterized in that the single-stranded wild-type hirudin gene or a single-stranded DNA comprising the wild-type hirudin gene is hybridized to an oligodeoxyribonucleotide primer which is complementary to the region of the hirudin gene to be mutated except for mismatch(es) that direct(s) the mutation, the hybridized oligodeoxyribonucleotide is used as a primer to initiate the synthesis of the complementary DNA strand, e.g. via PCR, the resulting (partially) double-stranded DNA is transformed into a recipient microorganism strain, the microorganism strain is cultivated and transformants containing DNA with the modified hirudin gene are selected.

In a preferred form two oligodeoxynucleotide primers (1) and (4) are used that are complementary to nucleotide sequences upstream and downstream of the desired sequence for amplification of the template DNA; and two internal primers (2) and (3) are used that are partly complementary to each other and both cover the site of mutation. The PCR primers (1) and (3) and the primers (2) and (4) are used pairwise in separate reactions to amplify parts of the template DNA and to introduce the mutation. In a second reaction both products are mixed and amplified with primers (1) and (4).

The wild-type hirudin gene is preferably contained in a plasmid, for example a plasmid described in EP-A-143 081 or EP-A-340 170. For mutagenesis the hirudin gene is advantageously isolated from the plasmid, for example by restriction endonuclease digestion resulting in a double-stranded DNA comprising the hirudin gene and optionally other functions linked thereto, for example promoter, signal peptide DNA etc., and having sticky ends, and amplified via PCR or ligated to a suitable restriction fragment of the replicative form (RF) of a single-stranded DNA phage, such as a derivative of phage M13, e.g., M13mp8 or M13mp9. Competent microorganisms, e.g., Ca-treated cells of an *E. coli* strain, are transfected with the hybrid phage vector and single-stranded phage DNA containing the inserted hirudin gene is isolated from the supernatant of the cultured cells. To this template the mismatch (mutagenic) oligodeoxyribonucleotide primer is hybridized.

Some of the methods described in the literature depend on the enzymatic extension of the mutagenic primer along the circular template followed by ligation to produce a covalently closed double-stranded circular molecule having the mutation(s) in the newly synthesized strand. Due to the generally low efficiency of this process a modified procedure has been developed (K. Norris et al., Nucl. Acids Res. (1983), 11, 5103) in which a second primer is used. In the case of an M13 phage vector a universal M13 sequencing primer is preferably used (EP-A-225 286).

Hybrid vectors containing DNA sequences coding for desulphatohirudin muteins

The invention relates also to hybrid vectors comprising a promoter and a DNA sequence coding for a human desulphatohirudin mutein in which one or more of the amino acids is (are) replaced by one or more amino acids capable of forming bonds to a further desulphatohirudin or a linker, which DNA sequence is under transcriptional control of said promoter.

The hybrid vectors according to the invention are selected from the group consisting of a hybrid plasmid and a linear DNA vector and are further selected depending on the host organism envisaged for transformation.

Promoters for yeast which are the most preferred host organisms according to the present invention are derived from the genomic DNA of yeast, especially of *Saccharomyces cerevisiae*. Preferably, the promoter of a highly expressed yeast gene is used for the expression of desulphatohirudin mutants. Thus, the promoter of the TRP1 gene, the ADHI or ADHII gene, acid phosphatase (PHO5) gene, CUP1 gene, isocytochrome c gene, or a promoter of the genes coding for glycolytic enzymes, such as TDH3, glyceraldehyde-3-phosphate dehydrogenase (GAPDH), a shortened version of GAPDH (GAPFL) which is preferred, 3-phosphoglycerate kinase (PGK), hexokinase, pyruvate decarboxylase, phosphofructokinase, glucose-6-phosphate isomerase, 3-phosphoglycerate mutase, pyruvate kinase, triosephosphate isomerase, phosphoglucose isomerase, invertase and glucokinase genes, or a promoter of the yeast mating pheromone genes coding for the a- or α-factor, can be used. Preferred vectors of the present invention contain promoters with transcriptional control. Promoters of this type, e.g. the promoter of the PHO5 or the CUP1 gene, can be turned on or off by variation of the growth conditions. For example, the PHO5 promoter can be repressed or derepressed at will, solely by increasing or decreasing the concentration of inorganic phosphate in the medium. Thus, the promoter can be repressed during the exponential growth phase of the yeast and may be turned on (derepressed) only during early stationary phase at maximal cell density allowing expression of the gene controlled by the PHO5 promoter. The CUP1 promoter can be turned on by the addition of $Cu^{2+}$-ions to the medium, e.g., in the form of a copper salt.

In the hybrid vectors of the present invention, the promoter is operably linked to the mutant hirudin coding region so as to ensure effective expression of the desulphatohirudin mutein. In the preferred embodiment of the present invention, especially if yeast is used as the host organism, a signal sequence is included in the construction. Suitable signal sequences are those of secreted yeast gene products, e.g., the PHO5, invertase or α-factor signal sequences, or the hirudin signal sequence. Alternatively, fused signal sequences may be constructed by in frame ligating part of the signal sequence of the gene naturally linked to a yeast promoter, with part of the hirudin signal sequence. Those combinations are favored which allow a precise cleavage between the signal peptide and the mature hirudin amino acid sequence. Additional sequences, such as pro-or spacer-sequences which may or may not carry specific processing signals can also be included in the constructions to facilitate accurate processing of precursor molecules. Alternatively fused proteins can be generated containing internal processing signals which allow proper maturation in vivo or in vitro. Preferably, the processing signals contain a Lys-Arg residue, which is recognized by a yeast endopeptidase located in the Golgi membranes. Upon expression of the mutant hirudin gene, the gene product enters the secretory pathway and is transported to the periplasmic space. If further excretion through the cell wall into the culture broth can be achieved, a considerable increase in yields should be possible. Also the recovery process can be simplified with no cells to be disrupted.

Preferably, the hybrid vectors according to the present invention comprise also the 3'-flanking sequence of a gene which contains the proper signals for transcription termination and polyadenylation. Suitable 3'-flanking sequences are for example those of the gene naturally linked to the promoter used, or 3'-flanking sequences of other yeast genes, e.g., of the PHO5 gene.

In the preferred hybrid plasmids according to the invention, the additional DNA sequences carry a yeast replication origin and a selective genetic marker for yeast. Hybrid plasmids containing a yeast replication origin, e.g. an autonomously replicating segment (Ars), are extrachromosomally maintained within the yeast cell after transformation and are autonomously replicated upon mitosis. Hybrid plasmids containing sequences homologous to yeast 2μ plasmid DNA can be used as well. These hybrid plasmids will get integrated by recombination into 2μ plasmids already present within the cell or will replicate autonomously. 2μ sequences are especially suitable for high-frequency transformation plasmids and give rise to high copy numbers.

In addition, the preferred hybrid plasmids according to the invention may include a DNA sequence as part of a gene present in the host yeast chromosome (e.g. the PHO5 gene or its promoter linked to the mutant hirudin coding region). By virtue of the homologous sequence, which should amount to a stretch of about 20 to 100 deoxynucleotides, the whole plasmid or linear fragments thereof can be stably incorporated into the host chromosome by recombination. Thus, during propagation the progeny cells will retain the introduced genetic material even without selective pressure.

As to the selective gene marker for yeast, any marker gene can be used which facilitates the selection for transformants due to the phenotypic expression of the marker. Suitable markers for yeast are particularly those expressing antibiotic resistance or, in the case of auxotrophic yeast mutants, genes which complement host lesions. Corresponding genes confer, for example, resistance to the antibiotic cycloheximide or provide for prototrophy in an auxotrophic yeast mutant, for example the URA3, LEU2, HIS3 or TRP1 gene. It is also possible to employ as markers structural genes which are associated with an autonomously replicating segment providing that the host to be transformed is auxotrophic for the product expressed by the marker.

Advantageously, the additional DNA sequences which are present in the hybrid plasmids according to the invention also include a replication origin and a selective genetic marker for a bacterial host, especially *Escherichia coli*. There are useful features which are associated with the presence of an *E. coli* replication origin and an *E. coli* marker in a yeast hybrid plasmid. Firstly, large amounts of hybrid plasmid DNA can be obtained by growth and amplification in *E. coli* and, secondly, the construction of hybrid plasmids is conveniently done in *E. coli* making use of the whole repertoire of cloning technology based on *E. coli*. *E. coli* plasmids, such as pBR322 and the like, contain both *E. coli* replication origin and *E. coli* genetic markers conferring resistance to antibiotics, for example tetracycline and ampicillin, and are advantageously employed as part of the yeast hybrid vectors.

The additional DNA sequences which contain, for example, replication origin and genetic markers for yeast and a bacterial host (see above) are hereinafter referred to as "vector DNA" which together with the yeast promoter and the mutant hirudin coding region is forming a hybrid plasmid according to the invention.

The preferred hybrid vectors of the present invention are prepared by methods known in the art, for example by linking a yeast promoter, a mutant hirudin coding region, the 3' flanking sequence of a yeast gene and optionally vector DNA.

For the preparation of hybrid plasmids, conveniently mapped circular vector DNA, for example bacterial plasmid DNA or the like (see above), having at least one restriction site, preferably two or more restriction sites, can be employed. Advantageously, the vector DNA already contains replication origins and gene markers for yeast and/or a bacterial host. The vector DNA is cleaved using an appropriate restriction endonuclease. The restricted DNA is ligated to the DNA fragment containing the yeast promoter and to the DNA segment coding for the desulphatohirudin mutein. Prior to or after linking of the promoter and the mutant hirudin coding region (or simultaneously as well), it is also possible to introduce replication origins and/or markers for yeast or a bacterial host. At all events, the restriction and ligation conditions are to be chosen in such a manner that there is no interference with the essential functions of the vector DNA and of the promoter. The hybrid vector may be built up sequentially or by ligating two DNA segments comprising all sequences of interest.

Various techniques may be used to join DNA segments in vitro. Blunt ends (fully base-paired DNA duplexes) produced by certain restriction endonucleases may be directly ligated with T4 DNA ligase. More usually, DNA segments are linked through their single-stranded cohesive ends and covalently closed by a DNA ligase, e.g. T4 DNA ligase. Such single-stranded "cohesive termini" may be formed by cleaving DNA with another class of endonucleases which produce staggered ends (the two strands of the DNA duplex are cleaved at different points at a distance of a few nucleotides). Single strands can also be formed by the addition of nucleotides to blunt ends or staggered ends using terminal transferase ("homopolymeric tailing") or by simply chewing back one strand of a blunt-ended DNA segment with a suitable exonuclease, such as λ exonuclease. A further approach to the production of staggered ends consists in ligating to the blunt-ended DNA segment a chemically synthesized linker DNA which contains a recognition site for a staggered-end forming endonuclease and digesting the resulting DNA with the respective endonuclease.

The components of the hybrid vector according to the invention, such as the yeast promoter, structural gene for the mutant hirudin optionally including a signal sequence, transcription terminator, the replication system etc., are linked together in a predetermined order to assure proper function. The components are linked through common restriction sites or by means of synthetic linker molecules to assure proper orientation and order of the components.

A linear DNA vector is made by methods known in the art, e.g. linking the above yeast promoter to the mutant hirudin coding region in such a manner that the mutant hirudin coding region is controlled by said promoter, and providing the resulting DNA with a DNA segment containing transcription termination signals derived from a yeast gene.

Joining of the DNA segments may be done as detailed above, viz. by blunt end ligation, through cohesive termini or through chemically synthesized linker DNAs.

In particular, in order to be efficiently expressed, the mutant hirudin gene must be properly located with respect to sequences containing transcriptional (yeast promoter) and translational functions (ribosome binding sites). Firs fly, the ligation of the DNA segment comprising the promoter with the mutant hirudin coding region has to be achieved in the proper orientation. If two orientations are possible the correct one is determined by conventional restriction analysis. Hybrid vectors containing an incorrectly oriented mutant hirudin gene insert are re-oriented by excising the gene insert with a suitable restriction endonuclease and re-ligating the gene with the hybrid vector fragment. In any case improper orientation is avoided by ligating two DNA segments each with different restriction sites at their ends. Furthermore, the construction of the hybrid vector should be done in such a way that it allows correct transcription initiation and termination. As to the latter point, the transcript should preferably end in a DNA sequence derived from yeast chromosomal DNA or yeast 2μ plasmid. Secondly, a proper reading frame must be established. Ordinarily, the nucleotide sequence of the promoter region and the mutant hirudin coding region is known prior to ligation or can easily be determined so that there are no problems in establishing the correct reading frame.

If the expression of the mature desulphatohirudin mutein for accumulation in the cytoplasm is desired, signal sequences or parts thereof optionally following the promoter region and/or optionally preceding the mature mutant hirudin coding region have to be eliminated, for example by digestion with an exonuclease, e.g. with Bal31. A preferred region for directly joining a yeast promoter to the mutant hirudin coding sequence is between the major mRNA start site and the ATG of the gene naturally linked to the yeast promoter. For a junction in this region the mutant hirudin coding sequence should have its own ATG for translation initiation, or else it has to be provided with an additional synthetic oligonucleotide. The yeast promoter may also be linked to the mutant hirudin coding sequence by means of a synthetic oligodeoxyribonucleotide as a connecting molecule. Thus, the promoter region may be, if possible, restricted near its 3'-terminus so that it lacks a predetermined number of base pairs. Analogously, the mutant hirudin coding sequence may be restricted near its 5'-terminus. A synthetic oligodeoxynucleotide can then be constructed in such a way that, when joining the yeast promoter and the mutant hirudin coding sequence via the connecting oligodeoxynucleotide, the missing base pairs are restored including an ATG translation initiation signal and the mutant hirudin coding sequence is in the proper reading frame relative to the ATG initiation codon.

If only a desulphatohirudin fragment is used the production is dependent on the length of said fragment. Normally, heterologous proteins with less than 20 amino acids cannot be expressed and isolated in sufficient mounts from natural hosts like *E. coli* and *S. cerevisiae*. A possible method for the expression of small proteins such as the carboxyterminal fragment of desulphatohirudin consists in fusing the small protein in question in frame to another protein thus creating a fusion protein. Several methods have been developed to liberate the desired protein from its fusion protein (Nishikawa et al., Protein Engineering 1, 487–492 (1987); Gardella et al., J. Biol. Chem. 265, 15854–15859, (1990); Altman et al., Protein Engineering 4, 593–600 (1991)). Possible hosts are fungi like yeasts, preferably *S. cerevisiae*, or bacteria like *E. coli*.

Suitable endogenous fusion partners are highly expressed proteins. Preferred are proteins like eglin, β-galactosidase, β-lactamase, several proteins involved in the tryptophan synthesis in *E. coli*, protein A or chloramphenicol acetyl transferase. In *S. cerevisiae* chimetic ubiquitin fusion proteins are preferably used (Sabin et al. Biotechnology 7, 705–709 (1989).

The desired carboxyterminal fragment of desulphatohirudin has to be removed from the fusion partner after expression and purification of the fusion protein. If there is no natural cleavage site between the desired fragment and the fusion partner, this is generally done by means of a linker sequence linking the desired fragment to the fusion partner and containing a cleavage site which can selectively be cleaved by chemical or enzymatic means. Such cleavage sites include, for example, a methionyl radical which is susceptible to the attack of cyanogen bromide, a polypeptide chain including the tetrapeptidyl radical Asp-Asp-Asp-Lys which is cleaved by enterokinase after Lys or any other cleavage site susceptible to a specific cleavage with enzymes like V8 protease, trypsin, peptidase yscα or yscF.

Another possibility for the production of short fragment is the synthesis with a peptide synthesizer.

If the desulphatohirudin mutein or derivative is produced by a yeast strain using a expression cassette including a signal sequence, the produced desulphatohirudin is predominantly (i.e. more than 90%) secreted into the culture broth. The desulphatohirudin can be isolated therefrom by conventional means. For example, the first step consists usually in separating the cells from the culture fluid by means of centrifugation. The resulting supernatant can be enriched for desulphatohirudin by treatment with polyethyleneimine so as to remove most of the non-proteinaceous material, and precipitation of the proteins by saturating the solution with ammonium sulphate. Host proteins, if present, can also be precipitated by means of acidification with acetic acid (for example 0.1%, pH 4–5). A further enrichment of desulphatohirudin can be achieved by extracting the acetic acid supernatant with n-butanol. Other purification steps include, for example, desalination, chromatographic processes, such as ion exchange chromatography, gel filtration chromatography, partition chromatography, HPLC, reversed phase HPLC and the like. The separation of the constituents of the mixture is also effected by dialysis, according to charge by means of gel electrophoresis or carrier-free electrophoresis, according to molecular size by means of a suitable Sephadex column, by affinity chromatography, for example with antibodies, especially monoclonal antibodies, or with thrombin coupled to a suitable carrier for affinity chromatography, or by other processes, especially those known from the literature. In general, only a few purification steps are required in order to get a desulphatohirudin product which is essentially free of contaminants.

The test with anti-desulphatohirudin or anti-desulphatohirudin antibodies (for example monoclonal antibodies), the thrombin test (M. U. Bergmeyer (ed.), Methods in Enzymatic Analysis 1983, Vol. II, p. 314–316, Verlag Chemie, Weinheim (FRG)) or the blood coagulation test (F. Markwardt et al., Thromb. Haemost. (1982), 47, 226) can be used to detect the desulphatohirudin activity during the isolation and purification steps. It is also possible to use chromatographical means, such as HPLC.

It is therefore an object of the invention to provide an expression cassette for a desulphatohirudin according to the invention, consisting of a promoter operably linked to a first DNA sequence encoding a signal peptide linked in the proper reading frame to a second DNA sequence coding for said desulphatohirudin mutein or derivative, and a DNA sequence with the transcription termination signals.

It is a further object of the invention to provide a method for the production of such desulphatohirudin conjugates consisting essentially of two to four desulphatohirudin muteins or derivatives, consisting of production of a suitable desulphatohirudin monomer e.g. by expression of a suitable desulphatohirudin in a suitable host, isolation of the desulphatohirudin, protection of the reacitve amino acid side chains if necessary, linking of the desulphatohirudin monomer to a suitable linker or directly linking of two desulphatohirudin monomeres together e.g. via a disulfide bond.

Pharmaceutical compositions

The novel desulphatohirudin conjugates obtainable in accordance with the present invention have valuable pharmacological properties and can, like monomeric desulphatohirudin extracted from leeches, be used prophylactically or, especially, therapeutically.

The desulphatohirudin conjugates according to the invention are, like natural hirudin, potent inhibitors of thrombin. They have, for example, a $K_i$ value of $10^{-9}$M to $10^{-13}$M. The desulphatohirudin conjugates are completely specific to thrombin and exhibit no interactions with other proteinases of the blood coagulation system. The toxicity is extremely low. Similarly, no hypersensitivity reactions or allergic reactions are observed. Because of the increased plasma half life of the desulphatohirudin conjugates, the administration of the daily dose of desulphatohirudin in a single portion is possible.

The novel desulphatohirudin conjugates according to the invention can therefore be used analogously to natural hirudin for the therapy and prophylaxis of thromboses and thromboembolisms, including the prophylaxis of post-operative thromboses, for acute shock therapy (for example for septic or polytraumatic shock), for the therapy of consumption coagulopathies, in haemodialyses, haemoseparations and in extracorporeal blood circulation.

The invention relates also to pharmaceutical compositions that contain a therapeutically effective amount of at least one of the compounds according to the invention or a pharmaceutically acceptable salt thereof, optionally together with a pharmaceutically acceptable carrier and/or adjuncts.

These compositions can be used especially in the above-mentioned indications, when they are administered, for example, parenterally, such as intravenously, intracutaneously, subcutaneously or intramuscularly.

The invention relates also to the use of the novel compounds according to the invention and to pharmaceutical compositions containing them for the prophylactic and therapeutic treatment of the human or animal body, especially for the above-mentioned clinical syndromes, especially for inhibiting the coagulation of blood inside and outside the human or animal body.

The dosage depends especially on the specific form of administration and on the purpose of the therapy or prophylaxis. The size of the individual doses and the administration regime can best be determined by way of an individual judgement of the particular case of illness; the methods of determining relevant blood factors required for this purpose are familiar to the person skilled in the art. Normally, in the case of an injection the therapeutically effective amount of the compounds according to the invention is in a dosage range of from approximately 0.005 to approximately 0.1 mg/kg body weight. A range of from approximately 0.01 to approximately 0.05 mg/kg body weight is preferred. The administration is effected by intravenous, intramuscular or subcutaneous injection. Accordingly, pharmaceutical compositions for parenteral administration in single dose form contain per dose, depending on the mode of administration, from approximately 0.4 to approximately 7.5 mg of the compound according to the invention. In addition to the active ingredient these pharmaceutical compositions usually also contain a buffer, for example a phosphate buffer, which is intended to keep the pH value between approximately 3.5 and 7, and also sodium chloride, mannitol or sorbitol for adjusting the isotonicity. They may be in freeze-dried or dissolved form, it being possible for solutions advantageously to contain an antibacterially active preservative, for example from 0.2 to 0.3% 4-hydroxybenzoic acid methyl ester or ethyl ester.

Another embodiment of the invention concerns an aqueous formulation comprising water, at least one of the compounds according to the invention and calcium, magnesium or zinc ions in the form of a water insoluble salt.

The water insoluble salt is preferably a phosphate as they are very insoluble.

This formulation may have a pH of from 4 to 11, preferably from 5 to 9. The concentration of the metal salt may be from 100 mM to 600 mM, preferably from 100 mM to 300 mM and most preferably about 150 mM. If the concentration is higher than a usable physiological concentration, the formulation may be diluted to physiological concentration before use. The concentration of the compounds according to the invention may be from 1 to 600 mg/ml, preferably from 20 to 80 mg/ml. If a high concentration is present it may be diluted, e.g. to 20 to 80 mg/ml range before use.

The particle size of the water insoluble salt may be from 10 to 30 μm diameter, preferably from 10 to 20 μm.

This formulation may be prepared by precipitating the water insoluble salt in situ in an aqueous solution of the compounds according to the invention. For example the chloride of the chosen metal (Ca, Mg or Zn) may be mixed with alkali metal phosphate. The pH of the resulting formulation may then be adjusted using e.g. hydrochloric acid or sodium hydroxide as appropriate. The preferred metal for this formultation is zinc.

The formulations of the invention may also contain a sugar such as sucrose, trehalose or, preferably, mannitol.

In addition to the compositions described above that are intended for direct medicinal use in the body of a human or an animal, the present invention relates also to pharmaceutical compositions for medicinal use outside the living body of humans or animals. Such compositions are used especially as anticoagulant additives to blood that is being subjected to circulation or treatment outside the body (for example extracorporeal circulation or dialysis in artificial kidneys), preservation or modification (for example haemoseparation). Such compositions, such as stock solutions or alternatively compositions in single dose form, are similar in composition to the injection compositions described above; however, the amount or concentration of active ingredient is advantageously based on the volume of blood to be treated or, more precisely, on its thrombin content. In this connection it must be borne in mind that the active ingredients according to the invention (in free form) completely deactivate approximately 5 times the amount by weight of thrombin, are physiologically harmless even in relatively large amounts, and are eliminated from the circulating blood rapidly even in high concentrations so that there is no risk of overdose, even, for example, during transfusions. Depending on the specific purpose, the suitable dose is from approximately 0.01 to approximately 1.0 mg of the active ingredient/liter of blood, although the upper limit may still be exceeded without risk.

BRIEF DESCRIPTION OF THE DRAWINGS

In the following experimental part various embodiments of the present invention are described with reference to the accompanying drawings in which.

EXPERIMENTAL PROCEDURES

Figure 1:
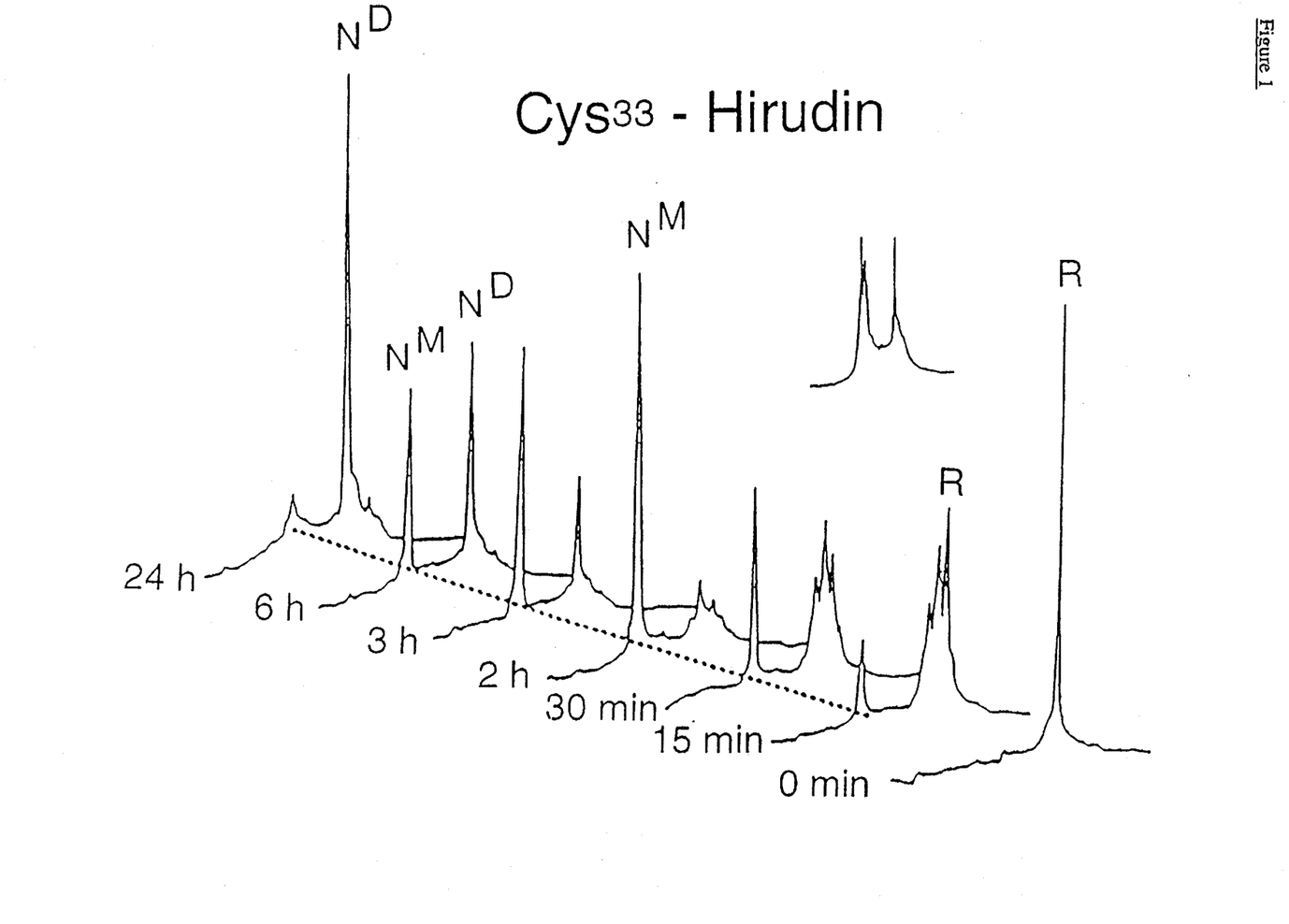
FIG. 1 is a schematic illustration of the refolding of the $Cys^{33}HV1$—$Cys^{33}HV1$ dimmers.

All DNA manipulations are—if not otherwise noted—carried out according to standard protocols (e.g. Maniatis, T. et al.: Molecular cloning: a laboratory manual. Cold Spring Harbor Laboratory, Cold Spring Harbor, N.Y. (1982).

EXAMPLE 1: Construction of plasmid pDP34/ GAPFL-YHIR (CYS33):

The expression in yeast (*Saccharomyces cerevisiae*) of desulphatohirudin-$Cys^{33}$, a mutant of the recombinant desulphatohirudin derivative 1 (HV1) (J. Dodt et al., FEBS Lett. 165 (1984), 180–184) with cysteine replacing aspartic acid at amino acid position 33, is achieved by changing the nucleotide sequence coding for desulphatohirudin. The method of Polymerase Chain Reaction (PCR) ("PCR Protocols: A guide to methods and applications" M. A. Innis, D. H. Gelfand, J. J. Sninsky, T. J. White (eds.). Academic Press, N.Y., 1990) is used to replace GAC with TGT in the expression cassette for the mutant desulphatohirudin. TGT codes for cysteine and therefore leads to the expression of desulphatohirudin-$Cys^{33}$ ($Cys^{33}HV1$).

The following PCR primers are used:

| (SEQ ID NO: 1, SEQ ID NO:2, SEQ ID NO:3, SEQ ID NO:4) | |
|---|---|
| | complementary to nucleotide positions of template DNA |
| (1) 5'-TCGGTCGACGCTCTCCCTTATGCG-3' | 7492–7494, 1–21 |
| (2) 5'-TTGGGTTCTTGTGGTGAAAAGAACCAATGTG-3' | 626–656 |
| (3) 5'-CTTTTCACCACAAGAACCCAAGATACACTTG-3' | 646–616 |
| (4) 5'-GCCAAGCTTGGCTGCAGATTTTAATC-3' | 1122–1100 |

The oligodeoxynucleotide primers are complementary to nucleotide sequences (see above) in the template DNA pJDB207/GAPFL-YHIR (EP-A-340 170) SEQ ID NO: 5. Primers (1) and (4) are the upstream and downstream primers for amplification of the template DNA; primers (2) and (3) are the internal primers which are partly complementary to each other and both cover the site of mutation (underlined). The PCR primers (1) and (3) and primers (2) and (4) are used pairwise in separate reactions to amplify parts of the template DNA and to introduce the mutation. Both PCR products overlap in the region of the mutation. In a second reaction both products are mixed and amplified with primers (1) and (4).

0.1 mg of template DNA of plasmid pJDB207/GAPFL-YHIR (EP-A-340 170) are mixed with 1 mg each of the primers (1) and (3) and alternatively with primers (2) and (4) for amplification of the corresponding DNA fragments according to standard PCR protocols (see above) using 30 cycles with 1 min. for DNA synthesis at 72° C., 10 sec. for DNA strand separation at 93° C. and 20 sec. for annealing at 50° C. The DNA fragments are purified by phenol extraction and precipitated in ethanol.

The second overlap-extension reaction contains 0.1 mg each of the PCR products amplified in the first reaction (see above) and 1 mg each of the PCR primers (1) and (4). 30 cycles with 1,5 min. for DNA synthesis at 72° C., 20 sec. for strand separation at 93° C. and 40 sec. for annealing at 50° C. are used.

The amplified DNA fragment is restricted with SalI and HindIII. The 1.1 kb SalI-HindIII fragment is cloned into SalI, HindIII cut vector pUC9 (Sigma®). Several clones are checked by restriction analysis and the insert of one correct clone is sequenced. The coding sequence of this clone contains the TGT codon coding for $Cys^{33}$.

The 1.1 kb SalI-HindIII insert is the mutant desulphatohirudin expression cassette comprising the 276 bp SalI-BamHI fragment of pBR322, a BamHI/BglII junction and the 194 bp GAPFL promoter with an EcoRI linker at position −5. The EcoRI site joins the promoter to the coding sequence of the PHO5 signal sequence and [$Cys^{33}$]HV1. The 3'terminal BamHI site is followed by the 377 bp PHO5 transcription terminator and a HindIII site.

The 1.1 kb expression cassette is cloned as a SalI-blunt end fragment into high copy number yeast expression vector pDP34 (DSM 4473) cut with BamHI (converted to blunt end by Klenow polymerase) and SalI. The resulting plasmid is referred to as pDP34/GAPFL-YHIR (CYS33). The sequences of the Cys$^{33}$HV1 part and the corresponding protein are given in SEQ ID NO: 7 and SEQ ID NO: 8.

EXAMPLE 2: Yeast transformation and fermentation

*Saccharomyces cerevisiae* strain TR1456 is constructed as disclosed in EP-A-341 215. Starting with *Saccharomyces cerevisiae* strain H449 (DSM 4413), in two subsequent series of experiments the two carboxypeptidases yscα and yscY are removed from strain H449 by disruption of their encoding genes KEX1 and PRC1, respectively. First, the gene encoding yscα, KEX1, is disrupted. For this purpose, strain H449 is transformed with a DNA fragment encoding the KEX1 gene, with the full URA3 gene inserted in the middle of the KEX1 coding region. Uracil prototrophic transformants are selected and tested for the absence of yscα activity. Next, the URA3 gene inserted at the KEX1 locus is disrupted by transformation with a plasmid containing a disrupted version of the URA3 gene, ura3Δ5 (see EP-A-341 215). Transformants which are uracil auxotrophic are selected and in the following step disrupted in their endogenous PRC1 gene coding for the carboxypeptidase yscY. The experiment is carried out in a totally analogous manner as described for the disruption of KEX1. The finally resulting isogenic derivative of strain H449 is called TR1456 and has the following genotype:

MATa, prb1, cps1, prc1::ura3, kex1::ura3, leu2-3,112, ura3Δ5, [cir$^{0}$].

Yeast strain TR 1456 is transformed with plasmid pDP34/ GAPFL-YHIR(CYS33) using the transformation protocol of Hinnen et al. (Proc. Natl. Acad. Sci. USA, 75 (1978) 1929–1933). Transformed yeast cells are grown under uracil selection. A single transformed yeast colony is referred to as

*Saccharomyces cerevisiae* TR 1456 /pDP34/GAPFL-YHIR- (CYS33).

The transformant is fermented for two successive precultures of 10 ml minimal medium lacking uracil, for the actual production run in complex medium without selection. Crude [Cys$^{33}$]HV1 is isolated from the culture broth as described in EP-A-340 170.

EXAMPLE 3: Preparation, unfolding and refolding of Cys$^{33}$HV1

[Cys$^{33}$]HV1 is expressed in yeast and excreted into the medium as described for native hirudin (Meyhack et al. (1987), Thromb. Res. Suppl., VII, 33). Cells are removed by centrifugation and proteins showing antithrombin activity are removed from supernatant by adsorbtion on XAD-7 resin. A mixture of active proteins is eluted with ammonium acetate buffer (0.2M, ph 8.5) and applied to a Q-sepharose fast-flow ion-exchange column. This column is eluted with ammonium formiate buffer (25 mM), using gradient elution from 0% A (buffer adjusted to pH 5.0 with formic acid) to 85% B (buffer adjusted to pH 3.0 with formic acid and containing 0.5M sodium chloride) within 50 min. Fractions showing antithrombin activity are pooled and lyophilized to dryness.

The crude [Cys$^{33}$]HV1 (4 mg) is reduced for 2 h at 23° C. in 0.75 ml of Tris-HCl buffer (0.5M, pH 8.4) containing 5M guanidine hydrochloride (GdmCl) and 0.1M dithiothreitol. The sample is passed through a PD-10 column (Pharmacia) equilibrated in 50 mM sodium bicarbonate buffer, pH 8.3. Reduced/denatured sample is collected in 1.2 ml and immediately diluted with the same sodium bicarbonate buffer to a final concentration of 1 mg/ml (140 mM). The folding is carried out at 23° C. and folding intermediates are trapped in a time course manner by acidifying aliquots of folding sample with 2 volumes of 4% trifluoroacetic acid.

EXAMPLE 4: HPLC characterization of the folding intermediates

[Cys$^{33}$]HV1 is refolded in 50 mM $NaHCO_3$ (pH 8.3) at 23° C. (see FIG. 1). The folding intermediates are trapped by acid in a time course manner and analyzed by HPLC using the following conditions:

Column: Vydac C-18 for peptides and proteins, 5 mm;

Solvent A: water containing 0.1% trifluoroacetic acid;

Solvent B: acetonitrile/water (9:1, v/v) containing 0.1% trifluoroacetic acid.

Gradient: 24% to 43% solvent B linear in 20 min.;

Detection: at 214 nm.

The reduced/denatured (R) Cys$^{33}$HV1 is eluted at 17.7 min.

"NM" is active Cys$^{33}$HV1 monomer (13.5 min.).

"ND" is Cys$^{33}$HV1 dimer.

Inset in FIG. 1 is crude [Cys$^{33}$]HV1 analyzed by the same HPLC conditions.

The heterogeneity of the crude product arises from the improper folding after biosynthesis or sample destruction during the purification.

Active [Cys$^{33}$]HV1 monomer (NM) is formed first (FIG. 1) with a first order rate constant of 0.05±0.01 min.$^{-1}$ under the conditions described. Oxidation of Cys$^{33}$ between two active [Cys$^{33}$]HV1 monomers subsequently occurred and the dimer is generated. The folding is highly efficient and the yield is greater than 85–90%. At pH higher than 8.3, the folding proceeds at an even faster speed.

EXAMPLE 5: Characterization of the [Cys$^{33}$] desulphatohirudin monomer and dimer The amino acid composition is determined by the dimethylaminoazobenzene sulfonyl (dabsyl) chloride method (Chang et al. Anal. Biochem. (1991), 197, 52–58.), which allows direct quantization of the disulfide content. The amino acid sequence was analyzed by an Applied Biosystem Inc. 470A protein sequencer. The antithrombin activity of desulphatohirudin derivatives was assessed by their ability to inhibit α-thrombin from digesting Chromozym TH (Boehringer Mannheim), using the described protocol (Stone et al. Biochemistry (1986), 25, 4622–4628; Chatrenet et al. J. Biol. Chem. (1992), 267, 3038–3043). The molecular weight of desulphatohirudin is 13916, determined by the laser desorption ionization mass spectrometry using a home-built instrument (Boernsen et al. Chimia (1990), 44, 412–416).

The [Cys$^{33}$]HV1—[Cys$^{33}$]HV1 dimer contains no free cysteine as confirmed by amino acid analysis.

The measurement of thrombin inhibition is performed at the concentration of 1 nM of desulphatohirudin and 1.5 nM of α-thrombin, the dimer exhibits, at equal weight basis, essentially the same inhibitory activity as wild type desulphatohirudin (82±5%).

EXAMPLE 6: The dimer and monomer are interconvertible

Unlike the three intra disulfides of desulphatohirudin, the Cys$^{33}$—Cys$^{33}$ bond of the dimer is not stabilized by noncovalent interactions. It is therefore possible to selectively cleave the $Cys^{33}$—$Cys^{33}$ bond under mild reducing conditions without disrupting the three disulfides located within the active core domain. Experiments are carried out in order to find out an optimum condition which allows quantitative conversion of the dimer to the monomer. This can be achieved by using 0.5 to 2.5 mM of β-mercaptoethanol at room temperature. At higher concentration of β-mercaptoethanol, the monomer rapidly disintegrates as a consequence of the reduction of $Cys^6$–$Cys^{14}$, $Cys^{16}$–$Cys^{28}$ and $Cys^{22}$–$Cys^{39}$ disulfide bonds.

EXAMPLE 7: Pharmaceutical composition containing a desulphatohirudin dimer for parenteral administration The lyophilized $[Cys^{33}]HV1$-$[Cys^{33}]HV1$ dimer according to example 3 is dissolved in 0.9% NaCl solution to a final concentration of 0.2 mg/ml or 2 mg/ml. These solutions are sterilized by ultrafiltration (membranes with 0.22 μm pores).

The sterilized solutions can be used directly, for example, for intravenous administration.

EXAMPLE 8: Effect of subcutaneously administered Hirudin HV1 and $[Cys^{33}]HV1$-$[Cys^{33}]HV1$ dimer on ex vivo plasma APTT in the rat (APTT=activated partial thrombin time)

$[Cys^{33}]HV1$—$[Cys^{33}]HV1$ dimer is dissolved in saline to a concentration of 4.5 mg/ml and unmodified hirudin-monomer is dissolved in saline to a concentration of 3.0 mg/ml (these doses are chosen based on the in vitro results in order to achieve a similar effect on APTT at 1 h). Solutions are administered subcutaneously to rats (1 ml/kg). At various times after administration, blood (2 ml) is collected by cardiac puncture directly into one tenth volume trisodium titrate solution (3.8% w/v) and immediately mixed. The anticoagulated blood is centrifuged at 2500 g for 20 min to obtain platelet free plasma.

Plasma samples are assayed for APTT using standard methods on the Instrumentation Laboratory ACL 300R coagulometer. The method for APTT determination utilizes the Instrumentation Laboratory ellagic acid test kit—plasma (50 μl) is incubated with ellagic acid activating reagent (50 μl) at 37° C. for 5 min prior to the addition of calcium chloride solution (50 μl of 25 mM solution) and the time taken for the plasma clot is recorded automatically, the end point being determined optically by the light scattered when the fibrin network formed (see table 1).

TABLE 1

| Time (hours) | HV1 | $[Cys^{33}]$-$[Cys^{33}]HV1$ dimer |
|---|---|---|
| 0 | 1.00 ± 0.02 | 1.00 ± 0.02 |
| 1 | 2.44 ± 0.07 | 2.29 ± 0.08 |
| 4 | 1.43 ± 0.05 | 2.07 ± 0.25 |
| 6 | 0.95 ± 0.02 | 1.44 ± 0.02 |

The results are expressed as a multiple of the means control APTT value and presented as mean±standard error of the mean (n=5).

EXAMPLE 9: Pharmaceutical composition

Solution A contains 2.43M $ZnCl_2$, and 0.455M $Na_2HPO_4$ in water at pH 2.5, pH adjusted with HCl. Solution B consists of 0.6M NaOH, 0.25M NaCl. A solution C is made by mixing 2 parts of a stock solution of $[Cys^{33}]$ HV1—$[Cys^{33}]HV1$ dimer in water (80 mg/ml) with 1.05 parts of solution A (ratio 2:1.05, v/v). The formulation is obtained by mixing water, solution B, and solution C in the weight ratio of 0.66:0.1883:0.4, respectively.

Similar mixtures are made using $CaCl_2$ or $MgCl_2$ instead of $ZnCl_2$.

EXAMPLE 10: Pharmaceutical composition

Solution A1 containes 165 mM $ZnCl_2$, 2.11 mM $Na_2HPO_4$ and 37.8 mM HCl in water. Solution B1 contains 0.6N NaOH. $[Cys^{33}]HV1$-$[Cys^{33}]HV1$ dimer (powder) is added to 31.7 parts by volume solution A1, followed by 55 parts by volume mannitol solution (198 mM) and then 13.3 parts by volume solution B1. The solution becomes turbid as the depot is formed. $[Cys^{33}]HV1$—$[Cys^{33}]HV1$ dimer is used in an amount of 20 mg/ml water used. No pH adjustment is needed.

EXAMPLE 11: Determination of the kinetic parameters for inhibition of human thrombin by the $[Cys^{33}]HV1$—$[Cys^{33}]HV1$ dimer The concentration of the hirudin is determined by titration against 2.0 nM thrombin in presence of 200 μM D-Val-Leu-Arg-p-nitroanilide as described by Wallace et al., Biochemistry (1989), 28, 10079–10084.

Based on weight and a molecular mass of 7000 for one subunit, the reaction of active molecules is 0.97. This finding demonstrated that both molecules in the dimer are active.

The kinetic parameters of the $[Cys^{33}]HV1$—$[Cys^{33}]HV1$ dimer are determined from progress-curve experiments as described by Stone et al. Biochemistry (1986), 25, 4622–4628 and Braun et al. Biochemistry, (1988), 27, 6517–6522. For each determination, the formation of p-nitroaniline from D-Phe-pipecolyl-Arg-p-nitroanilide is monitored in six assays, one in absence of inhibitor and the others with different concentrations of inhibitor ranging from 10 to 60 pM for the $[Cys^{33}]HV1$—$[Cys^{33}]HV1$ dimer. The substrat concentration is 100 μM and the enzyme concentration is 20 pM.

The kinetic parameters are determined twice and values given in table 2 represent the weightened means of the estimates.

TABLE 2

| | Parameter | |
|---|---|---|
| Inhibitor | $10^8 k_1$ ($M^{-1} s^{-1}$) | $K_1$ (pM) |
| $[Cys^{33}]HV1$-$[Cys^{33}]HV1$ dimer | (0.51 ± 0.03) | 0.330 ± 0.038 |
| HV1 | (1.37 ± 0.03) | 0.237 ± 0.006 |

Deposition of microorganisms

The following microorganism strains were deposited at the Deutsche Sammlung von Mikroorganismen (DSM), Mascheroder Weg 1b, D-3300 Braunschweig (deposition dates and accession numbers given):

*Saccharomyces cerevisiae* H449: Feb. 18, 1988, DSM 4413;
*Escherichia coli* JM109/pDP34: Mar. 14, 1988, DSM 4473;

We claim:

1. A conjugate consisting of two to four residues of desulphatohirudin muteins or derivatives having hirudin activity wherein the conjugate is not a fusion protein, the residues of desulphatohirudin muteins or derivatives having hirudin activity are not connected via glutaraldehyde or carbodiimide, and wherein said residues are linked within the N-terminal domain of desulphatohirudin.

2. A conjugate according to claim 1, consisting of two residues of desulphatohirudin muteins or derivatives having hirudin activity.

3. A conjugate according to claim 1, consisting of two residues of desulphatohirudin muteins or derivatives, of HV1, HV2, or HV3 (PA), having hirudin activity.

4. A conjugate according to claim 1, consisting of two residues of desulphatohirudin HV1 muteins or derivatives having hirudin activity.

5. A conjugate according to claim 1, wherein the desulphatohirudins or desulphatohirudin derivatives are connected directly or via a linker group.

6. A conjugate according to claim 1, wherein two cysteines in the desulphatohirudin muteins or derivatives having hirudin activity are connected directly or via a linker group.

7. A conjugate according to claim 1, wherein the desulphatohirudin muteins or derivatives are connected directly via a disulfide bond.

8. A conjugate according to claim 1, wherein the monomers of the two desulphatohirudin muteins or derivatives, or the monomer of desulphatohirudin mutein or derivative and the linker group, are linked in the region between amino acid residues 7 to 50.

9. A conjugate according to claim 8, wherein the monomers of the two desulphatohirudin muteins or derivatives, or the monomer of desulphatohirudin mutein or derivative and the linker group, are linked in the region between amino acid residues 30 to 40.

10. A conjugate according to claim 1, comprising desulphatohirudins wherein one or more amino acids are replaced by one or more radicals capable of being crosslinked.

11. A conjugate according to claim 10, comprising desulphatohirudins wherein one amino acid of desulphatohirudin is replaced by an amino acid selected from the group consisting of aspartic acid, glutamic acid, lysine and cysteine.

12. A conjugate according to claim 11, comprising desulphatohirudins wherein one amino acid is replaced by cysteine.

13. A conjugate according to claim 12, comprising two desulphatohirudin HV1 wherein $Asp^{33}$ is replaced by Cys.

14. A desulphatohirudin HV1, wherein $Asp^{33}$ is replaced by Cys (SEQ ID NO: 8).

15. A first desulphatohirudin mutein or derivative, having hirudin activity, being capable of being crosslinked to a second desulphatohirudin mutein or derivative also having hirudin activity, wherein said second desulphatohirudin mutein or derivative is either the same as or different from the first desulphatohirudin mutein or derivative.

16. A method for preparing a pharmaceutical composition comprising combining the compound of claim 1 with conventional carriers.

17. A pharmaceutical composition comprising a conjugate consisting of two to four residues of desulphatohirudin muteins or derivatives according to claim 1, or which comprises said compounds together with conventional auxiliaries, typically carriers and diluents.

18. An aqueous formulation comprising water, a compound according to claim 1 and calcium, magnesium or zinc ions to form a water insoluble salt.

19. A formulation according to claim 18, wherein the water insoluble salt is a phosphate.

20. A formulation according to claim 18, wherein the concentration of the metal salt is from 100 mM to 600 mM.

21. A formulation according to claim 18, wherein the concentration of the compound according to claim 1 is from 1 to 600 mg/ml.

22. A formulation according to claim 18, wherein the particle size of the water insoluble salt is from 10 to 30 μm diameter.

23. A pharmaceutical composition comprising a therapeutically effective amount of at least one of the conjugates according to claim 1 or a pharmaceutically acceptable salt thereof for use in a method for the therapy and prophylaxis of thromboses and embolism.

24. An expression vector comprising an expression cassette for a desulphatohirudin according to claim 5, consisting of a promoter operably linked to a first DNA sequence encoding a signal peptide linked in the proper reading frame to a second DNA sequence coding for said desulphatohirudin mutein or derivative, and a DNA sequence with the transcription termination signals.

25. An expression cassette according to claim 24 wherein the promoter is the GAPFL or the CUP1 promoter.

26. An expression cassette according to claim 24 wherein the signal sequence is the PHO5 signal sequence.

27. An expression cassette according to claim 24 wherein the desulphatohirudin mutein or derivative is [$Cys^{33}$]HV1 (SEQ ID NO: 7).

28. An expression cassette according to claim 24 wherein the terminator is the PHO5 terminator.

29. Process for the production of a conjugate according to claim 1, consisting of expression of a suitable desulphatohirudin in a suitable host, isolation of the desulphatohirudin, protection of the reactive amino acid side chains if necessary, linking of the desulphatohirudins to a suitable linker or directly linking of two desulphatohirudins together.

30. A process according to claim 29 wherein the desulphatohirudins are linked via a disulfide bond.

31. A process according to claim 30, wherein the desulphatohirudins are unfolded and refolded after isolation.

32. A method for denaturing and renaturing desulphatohirudin to a biologically active polymeric or dimeric form comprising the steps:

denaturing desulphatohirudin as defined above with chaotropic agent, renaturing of the desulphatohirudin under refolding conditions, and linking of the desulphatohirudins by means of a linker or directly.

33. A method for the treatment of a human or animal in need of thrombin inhibition, said method comprising administering to the human or animal an effective amount of the conjugate of claim 1 in a pharmaceutically acceptable carrier.

* * * * *